United States Patent [19]

Hsu et al.

[11] Patent Number: 5,334,726
[45] Date of Patent: * Aug. 2, 1994

[54] ARYL TRIAZOLE HERBICIDES

[75] Inventors: Adam C. Hsu, Lansdale; Colin M. Tice, Elkins Park, both of Pa.

[73] Assignee: Rohm and Haas Company, Philadelphia, Pa.

[*] Notice: The portion of the term of this patent subsequent to Jun. 9, 2009 has been disclaimed.

[21] Appl. No.: 848,770

[22] Filed: Mar. 10, 1992

Related U.S. Application Data

[62] Division of Ser. No. 541,575, Jun. 21, 1990, Pat. No. 5,120,347.

[51] Int. Cl.$^5$ .................................. C07D 249/12
[52] U.S. Cl. ........................................ 548/263.2
[58] Field of Search ..................................... 548/263.2

[56]     References Cited

U.S. PATENT DOCUMENTS

| | | | |
|---|---|---|---|
| 3,514,466 | 5/1970 | Stahle | 548/263.2 |
| 4,775,688 | 10/1988 | Kane et al. | 548/263.2 |
| 4,946,856 | 8/1990 | Kane et al. | 548/263.2 |
| 4,948,417 | 8/1990 | Lindig et al. | 548/263.2 |
| 4,952,593 | 8/1990 | Kane et al. | 548/263.2 |
| 5,064,845 | 11/1991 | Hsu et al. | 548/263.2 |
| 5,120,347 | 6/1992 | Hsu et al. | 548/263.2 |
| 5,125,958 | 6/1992 | Poss | 548/263.2 |

OTHER PUBLICATIONS

Akita, et al., "1,2,4-Triazolin-5-one derivatives etc." CA 104:186423j (1986).

*Primary Examiner*—Patricia L. Morris
*Attorney, Agent, or Firm*—Joseph F. Leightner

[57]     ABSTRACT

This invention relates to herbicidal aryl triazoles having the structure

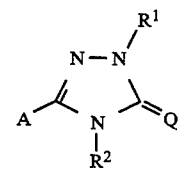

wherein A is phenyl or thienyl, Q is oxygen or sulfur and $R^1$ and $R^2$ are as defined within, compositions containing these compounds and methods of controlling weeds with these compounds.

2 Claims, No Drawings

ARYL TRIAZOLE HERBICIDES

This is a divisional of application Ser. No. 541,575, filed Jun. 21, 1990, now U.S. Pat. No. 5,120,347.

This invention relates to substituted aryl triazoles which show activity as herbicides, to herbicidal compositions which contain these compounds and to methods of controlling weeds with these herbicidal compositions.

BACKGROUND OF THE INVENTION

During the past years, there has been an intensified search for herbicides to control unwanted plants. Japanese Kokai 60:218379 discloses 1,4-di-(2-propynyl)-delta-2-1,2,4-triazolin-5-one derivatives having herbicidal activity. No mono-propynyl-substituted compounds are disclosed.

There remains a need for additional herbicidal agents which are as effective or more effective than presently existing compounds.

SUMMARY OF THE INVENTION

It has now been found that a class of substituted aryl triazoles of the formula

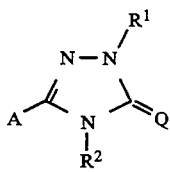

(I)

wherein

A is phenyl or thienyl;

Q is oxygen (O) or sulfur (S);

$R^1$ is alkyl, alkenyl, alkynyl, cycloalkyl, or haloalkyl; and $R^2$ is $(C_1-C_2)$alkyl, alkenyl, alkynyl, monohaloalkynyl, alkoxyalkyl, or monohaloalkyl;

provided $R^1$ and $R^2$ are not concurrently 2-propynyl or are not concurrently methyl or ethyl, possesses herbicidal activity.

In the above formula, alkyl means straight and branched alkyl groups, for example $(C_1-C_6)$alkyl such as methyl, ethyl, n-propyl, isopropyl, n-butyl, isobutyl, s-butyl or 1-ethylpropyl. Cycloalkyl is, for example, $(C_3-C_6)$ cycloalkyl such as cyclopropyl, cyclobutyl, cyclopentyl, cyclohexyl and includes cycloalkyl optionally substituted by $(C_1-C_4)$alkyl. Phenyl and thienyl are optionally substituted with one or two substituents such as $(C_1-C_3)$alkyl, halogen, methoxy or trifluoromethyl. Haloalkyl is, for example, fluoromethyl, difluoromethyl, trifluoromethyl, 2,2-difluoroethyl or 1-methyl-2,2,3,3-tetrafluoropropyl.

Halogen means fluorine, chlorine, bromine and iodine.

Alkoxy is, for example $(C_1-C_6)$alkoxy such as methoxy or ethoxy. Alkoxyalkyl is, for example, $(C_1-C_6)$alkoxy$(C_1-C_6)$alkyl such as methoxymethyl. Alkenyl is, for example, $(C_3-C_6)$alkenyl such as allyl. Alkynyl is, for example, $(C_3-C_6)$alkynyl such as 2-propenyl (propargyl). Monohaloalkynyl is, for example, monohalo$(C_3-C_6)$alkynyl such as 3-iodopropargyl or 3-bromopropargyl.

Preferably the compounds of the invention are herbicidal compounds of the formula

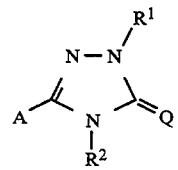

wherein

A is phenyl, 2-chlorophenyl, 2-fluorophenyl, 2-methoxyphenyl, 3-methylphenyl, 3-trifluoromethylphenyl, 3-halophenyl, 3-methoxyphenyl, 4-fluorophenyl, 2,5-dichlorophenyl, 2-thienyl or 3-thienyl;

Q is oxygen or sulfur;

$R^1$ is $(C_1-C_6)$alkyl, $(C_3-C_6)$alkenyl, $(C_3-C_6)$alkynyl, $(C_3-C_6)$cycloalkyl or halo$(C_1-C_6)$alkyl; and $R^2$ is $(C_1-C_2)$alkyl, $(C_3-C_6)$alkenyl, $(C_3-C_6)$alkynyl, monohalo$(C_1-C_6)$alkyl, monohalo$(C_3-C_6)$alkynyl, or $(C_1-C_6)$alkoxy$(C_1-C_6)$alkyl;

provided $R^1$ and $R^2$ are not concurrently 2-propynyl or are not concurrently methyl or ethyl.

In one class of compounds of the invention are herbicidal compounds wherein

A is phenyl, 2-fluorophenyl, 2-methoxyphenyl, 3-methylphenyl, 3-methoxyphenyl, 3-chlorophenyl, 3-fluorophenyl, 4-fluorophenyl, 3-bromophenyl, 2,5-dichlorophenyl or 2-thienyl;

Q is oxygen or sulfur; and $R^1$ is 2-propynyl and $R^2$ is $(C_1-C_2)$alkyl or halo$(C_1-C_6)$alkyl; or $R^2$ is 2-propynyl and $R^1$ is $(C_1-C_6)$alkyl, halo$(C_1-C_6)$alkyl or $(C_3-C_6)$cycloalkyl.

In the embodiment where $R^1$ is 2-propynyl, more preferably Q is oxygen, A is phenyl, 2-fluorophenyl, 2-methoxyphenyl, 3-methylphenyl, 3-methoxyphenyl 3-chlorophenyl, 3-fluorophenyl, 3-bromophenyl, 4-fluorophenyl or 2,5-dichlorophenyl, and $R^2$ is $(C_1-C_2)$alkyl.

Most preferably, $R^2$ is methyl or ethyl.

In the embodiment where $R^2$ is 2-propynyl, more preferably Q is oxygen, A is phenyl, 2-fluorophenyl, 3-fluorophenyl or 2-thienyl and $R^1$ is $(C_1-C_6)$alkyl, halo$(C_1-C_6)$alkyl or $(C_3-C_6)$cycloalkyl.

Most preferably A is phenyl, 2-fluorophenyl or 3-fluorophenyl and $R^1$ is t-butyl or A is phenyl and $R^1$ is n-propyl.

In another class of compounds of the invention are herbicidal compounds wherein

A is phenyl, 2-fluorophenyl, 2-methoxyphenyl, 3-methylphenyl, 3-methoxyphenyl 3-chlorophenyl, 3-fluorophenyl, 3-bromophenyl, 3-trifluoromethyl, 4-fluorophenyl, 2,5-dichlorophenyl, 2-thienyl or 3-thienyl;

Q is oxygen or sulfur;

$R^1$ is $(C_1-C_6)$alkyl; and $R^2$ is $(C_1-C_2)$alkyl, $(C_1-C_6)$alkoxy$(C_1-C_6)$alkyl, monohalo$(C_3-C_6)$alkynyl or monohalo$(C_1-C_6)$alkyl;

provided $R^1$ and $R^2$ are not concurrently methyl or ethyl.

In the embodiment where $R^2$ is monohalo$(C_3-C_6)$alkynyl, more preferably Q is oxygen, $R^1$ is $(C_1-C_6)$alkyl and A is phenyl.

Most preferably, $R^2$ is 3-bromopropargyl or 3-iodopropargyl.

In the embodiment where $R^2$ is $(C_1-C_2)$alkyl, $(C_1-C_6)$alkoxy$(C_1-C_6)$alkyl, or monohalo$(C_1-C_6)$alkyl, Q is oxygen.

More preferred are herbicidal compounds wherein A is phenyl, 3-trifluoromethylphenyl, 3-chlorophenyl or 3-thienyl; Q is oxygen; $R^1$ is t-butyl or n-propyl and $R^2$ is methyl, ethyl, methoxymethyl, 2-methoxyethyl or 2-fluoroethyl.

Most preferably, A is phenyl or 3-chlorophenyl, $R^1$ is t-butyl or n-propyl and $R^2$ is methoxymethyl or 2-methoxyethyl.

The compounds of the invention can be prepared by a variety of methods.

One suitable method comprises reacting an acyl formic acid 1 with a hydrazine in an aqueous or alcoholic solution with or without added acid such as hydrochloric acid at a temperature of from about 0° C. and about 100° C., preferably from about 15° C. to about 50° C. to yield an alkyl hydrazone which is then cyclized in the presence of diphenylphosphoryl azide to yield the triazolinone 2. Preferred solvents for the cyclization reaction are inert organic solvents such as benzene, xylene or toluene, preferably toluene. The reaction is carried out at a temperature of from about 0° C. to about 150° C., preferably from about 50° C. to about 120° C. The triazolinone is then alkylated in the presence of base to yield the compounds of the invention 3.

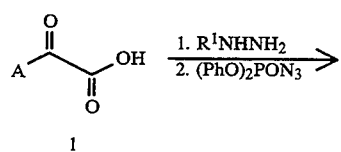

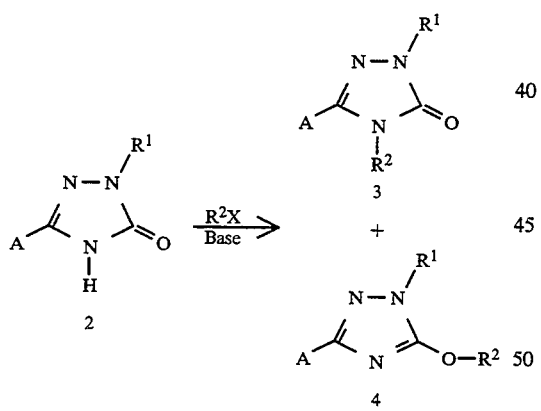

The alkylation reaction is carried out in an inert organic solvent such as ethyl acetate, toluene, benzene, xylene, ethers such as tetrahydrofuran and glyme, ketones such as acetone and 2-butanone, alcohols such as methanol and ethanol and dimethylformamide or mixtures thereof. The reaction is carried out at a temperature of from about 0° C. to about 150° C., preferably from about 50° C. to about 125° C. in the presence of a base such as potassium carbonate; sodium hydride; sodium alkoxides, for example sodium methoxide or sodium ethoxide; potassium hydroxide or sodium hydroxide.

Alternatively the compounds of the invention are prepared using an acyl semicarbazide 7, which is prepared either from a hydrazide 5 or a semicarbazide 6.

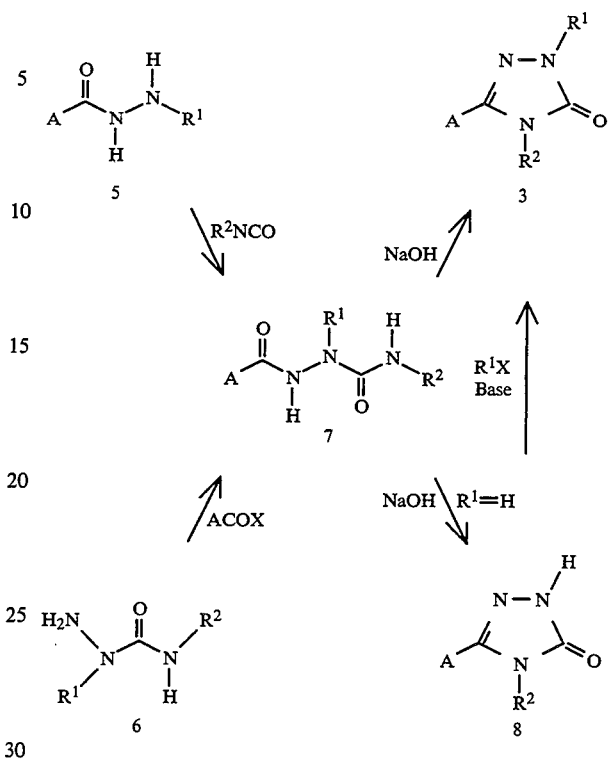

When starting from a hydrazide, the hydrazide is reacted with an isocyanate in an inert organic solvent such as ethyl ether, glyme, tetrahydrofuran, ethyl acetate, benzene, or toluene or mixtures thereof at a temperature of from about 0° C. to about 100° C., preferably from about 15° C. to about 50° C.

When starting from the semicarbazide, the semicarbazide is reacted with an acylating agent such as an acid chloride or anhydride in the presence of a base in an inert or substantially inert solvent or mixture of solvents to yield the desired acyl semicarbazide.

Suitable solvents for use in the above processes include water; alcohols such as methanol, ethanol, and isopropanol; hydrocarbons such as toluene, xylene, hexane and heptane; glyme; tetrahydrofuran; acetonitrile; pyridine; or haloalkanes such as methylene chloride or mixtures of these solvents.

Preferred solvents are water, toluene, methylene chloride or a mixture of these solvents.

Examples of bases for use in the above processes include tertiary amines such as triethylamine; pyridine; potassium carbonate; sodium carbonate; sodium bicarbonate; sodium hydroxide; or potassium hydroxide. Preferred bases are sodium hydroxide, potassium hydroxide or triethylamine.

The acyl semicarbazide is cyclized by heating the compound in a basic solution such as 5% sodium hydroxide or potassium hydroxide at a temperature between about 0° C. and about 150° C. preferably from about 50° C. to about 120° C.

When Q is sulfur instead of oxygen, the compounds can be prepared by reacting a hydrazide 5 with an isothiocyanate in a solvent

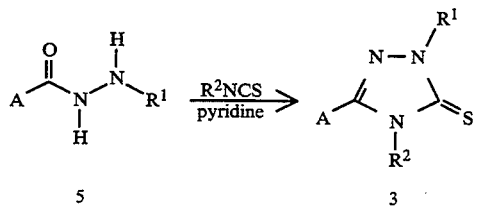

such as pyridine at a temperature of from about 0° C. and 150° C., preferably between about 50° C. and 100° C.

The following examples further illustrate this invention but are not intended to limit it in any way. In Table I, typical aryl triazoles are listed with their melting points. The proton NMR data are listed in Table II for those compounds for which no melting point is supplied. Specific illustrative preparations of the compounds are described after Table II.

TABLE I

| | $R^1$ | Q | $R^2$ | A | m.p. °C. |
|---|---|---|---|---|---|
| 1. | $C(CH_3)_3$ | O | $CH_2C\equiv CH$ | $C_6H_5$ | 87–89 |
| 2. | $C(CH_3)_3$ | O | $CH_3$ | $C_6H_5$ | 60–64 |
| 3. | $C(CH_3)_3$ | S | $CH_3$ | $C_6H_4\text{-}3\text{-}CF_3$ | Oil |
| 4. | $C(CH_3)_3$ | O | $CH_2CH_3$ | $C_6H_5$ | 53–54 |
| 5. | $C(CH_3)_3$ | O | $CH_2C\equiv CH$ | (2-thienyl) | 111–112.5 |
| 6. | $C(CH_3)_3$ | O | $CH_2CH=CH_2$ | $C_6H_5$ | 52–56 |
| 7. | $C(CH_3)_3$ | O | $CH_2CH_3$ | $C_6H_4\text{-}3\text{-}Cl$ | Oil |
| 8. | $C(CH_3)_3$ | O | $CH_2C\equiv CCH_3$ | $C_6H_5$ | 65–70 |
| 9. | $C(CH_3)_3$ | O | $CH_2OCH_3$ | $C_6H_5$ | 53–57 |
| 10. | $C(CH_3)_3$ | O | $CH_2CH_2OCH_3$ | $C_6H_5$ | Oil |
| 11. | $CH_2CF_3$ | O | $CH_2C\equiv CH$ | $C_6H_5$ | Oil |
| 12. | $CH_3$ | O | $CH_2C\equiv CH$ | $C_6H_5$ | Oil |
| 13. | $CH_2CH_2CH_3$ | O | $CH_2C\equiv CH$ | $C_6H_5$ | Oil |
| 14. | $CH(CH_3)CF_2CF_2H$ | O | $CH_2C\equiv CH$ | $C_6H_5$ | Oil |
| 15. | cyclohexylmethyl | O | $CH_2C\equiv CH$ | $C_6H_5$ | 108–110 |
| 16. | $CH_2CH_2CH_2CH_3$ | O | $CH_2C\equiv CH$ | $C_6H_5$ | 66–67 |
| 17. | $CH_2CH(CH_3)_2$ | O | $CH_2C\equiv CH$ | $C_6H_5$ | 62–63 |
| 18. | $CH_2CH_2CH_3$ | O | $CH_2C\equiv CCH_3$ | $C_6H_5$ | Oil |
| 19. | $CH_2C\equiv CH$ | O | $CH_2CH_3$ | $C_6H_5$ | Oil |
| 20. | $CH_2CH_3$ | O | $CH_2C\equiv CH$ | $C_6H_5$ | 89–90 |
| 21. | $CH_2C\equiv CH$ | O | $CH_2CH_3$ | $C_6H_4\text{-}3\text{-}CH_3$ | 78–80 |
| 22. | $CH_2CH_2CH_3$ | O | $CH_2CH_3$ | $C_6H_4\text{-}3\text{-}Cl$ | Oil |
| 23. | $CH_2C\equiv CH$ | O | $CH_2CH_3$ | $C_6H_4\text{-}3\text{-}Cl$ | 82–85 |
| 24. | $CH_2C\equiv CH$ | O | $CH_2CH_3$ | $C_6H_4\text{-}3\text{-}F$ | 57–60 |
| 25. | $CH_2C\equiv CH$ | O | $CH_2CH_3$ | $C_6H_4\text{-}3\text{-}Br$ | 91–93 |
| 26. | $CH_2C\equiv CH$ | O | $CH_2CH_3$ | $C_6H_4\text{-}2\text{-}F$ | 97–100 |
| 27. | $CH_2C\equiv CH$ | O | $CH_2CH_3$ | $C_6H_4\text{-}4\text{-}F$ | 62–65 |
| 28. | $CH_2C\equiv CH$ | O | $CH_2CH_3$ | $C_6H_4\text{-}3\text{-}OCH_3$ | 91–94 |
| 29. | $CH_2C\equiv CH$ | O | $CH_2CH_3$ | $C_6H_4\text{-}2\text{-}OCH_3$ | 100–105 |
| 30. | $CH_2C\equiv CH$ | O | $CH_2CH_3$ | $C_6H_3\text{-}2,5\text{-}(Cl)_2$ | 93–99 |
| 31. | $C(CH_3)_3$ | S | $CH_3$ | $C_6H_5$ | Oil |
| 32. | $CH_2CH_2CH_3$ | O | $CH_2CH_3$ | (2-thienyl) | Oil |
| 33. | $CH_2CH_2CH_3$ | O | $CH_2CH_2F$ | $C_6H_5$ | Oil |
| 34. | $C(CH_3)_3$ | O | $CH_2C\equiv CH$ | $C_6H_4\text{-}3\text{-}F$ | Oil |
| 35. | $C(CH_3)_3$ | O | $CH_2C\equiv CH$ | $C_6H_4\text{-}2\text{-}F$ | Oil |
| 36. | $CH_2C\equiv CH$ | O | $CH_3$ | $C_6H_4\text{-}3\text{-}Cl$ | 96–99 |
| 37. | $CH_2C\equiv CH$ | O | $CH_3$ | $C_6H_4\text{-}3\text{-}Br$ | 99–101 |
| 38. | $CH_2C\equiv CH$ | O | $CH_3$ | $C_6H_4\text{-}3\text{-}F$ | 78–80 |
| 39. | $CH_2C\equiv CH$ | O | $CH_3$ | $C_6H_4\text{-}2\text{-}F$ | 85–89 |
| 40. | $C(CH_3)_3$ | O | $CH_2C\equiv CCl$ | $C_6H_5$ | 118–126 |
| 41. | $C(CH_3)_3$ | O | $CH_2C\equiv CBr$ | $C_6H_5$ | 86–91 |

TABLE II

NMR DATA

| Cmpd. No. | Solvent | (200 MHz, delta Scale in ppm TMS Standard) |
|---|---|---|
| 3. | CDCl$_3$ | 1.85 (9H,s), 3.67 (3H,s), 7.80 (4H,m) |
| 7. | CDCl$_3$ | 1.26 (3H,t), 1.62 (9H,s), 3.80 (2H,q) 7.36–7.80 (4H,m) |
| 10. | CDCl$_3$ | 1.61 (9H,s), 3.28 (3H,s), 3.67 (2H,t) 3.90 (2H,t), 7.48 (3H,m), 7.70 (2H,m) |
| 11. | CDCl$_3$ | 2.39 (1H,t), 4.45 (2H,q), 4.53 (2H,d) 7.55 (3H,m), 7.79 (2H,m) |
| 12. | CDCl$_3$ | 2.37 (1H,t), 3.55 (3H,s), 4.50 (2H,d) 7.53 (3H,m), 7.75 (2H,m) |
| 13. | CDCl$_3$ | 1.00 (3H,t), 1.85 (2H,m), 2.37 (1H,t) 3.85 (2H,t), 4.53 (2H,d), 7.55 (3H,m) 7.78 (2H,m) |
| 14. | CDCl$_3$ | 1.63 (3H,d), 2.39 (1H,t), 4.50 (2H,d) 4.95 (1H,m), 5.95 (1H,tt), 7.53 (3H,m) 7.77 (2H,m) |
| 18. | CDCl$_3$ | 0.98 (3H,t), 1.77 (3H,t), 1.84 (2H,m) 3.83 (2H,t), 4.46 (2H,q), 7.52 (3H,m) 7.69 (2H,m) |
| 19. | CDCl$_3$ | 1.38 (3H,t), 2.44 (1H,t), 3.92 (2H,q) 3.92 (2H,q), 7.60 (5H,br s) |
| 22. | CDCl$_3$ | 1.00 (3H,t), 1.31 (3H,t), 1.85 (2H,m) 3.84 (4H,m), 7.50 (3H,m), 7.63 (1H,s) |
| 31. | CDCl$_3$ | 1.86 (9H,s), 3.60 (3H,s), 7.55 (5H,m) |
| 32. | CDCl$_3$ | 0.95 (3H,t), 1.30 (3H,t), 1.80 (2H,m) 3.75–3.95 (4H,m), 7.4 (2H,m), 7.63 (1H,s) |
| 33. | CDCl$_3$ | 0.95 (3H,t), 1.82 (2H,m), 3.80 (2H,t) 4.00 (2H,dt), 4.70 (2H,dt), 7.48 (3H,m) 7.62 (2H,m) |
| 34. | CDCl$_3$ | 1.65 (9H,s), 2.39 (1H,t), 4.50 (2H,d) 7.23 (1H,m), 7.55 (3H,m) |
| 35. | CDCl$_3$ | 1.65 (9H,s), 2.12 (1H,t), 4.45 (2H,d) 7.28 (2H,m), 7.57 (2H,m) |

EXPERIMENTAL

EXAMPLE 1

1-t-Butyl-3-phenyl-4-propargyl-1,2,4-triazolin-5-one a. Benzoylformic acid t-Butyl hydrazone A mixture of 296 grams (g) (2.37 mol) of t-butyl hydrazine hydrochloride, 20 milliliters (mL) of concentrated hydrochloric acid (HCl) and 2 liters (L) of water was stirred at room temperature to give a clear solution. Benzoylformic acid (400 g, 2.61 mol) was added in four equal portions at 3 minute intervals. The mixture was stirred overnight at room temperature and filtered. The solid collected was washed with water and dried in vacuo to furnish 520 g (99%) of the compound, mp 138°–139° C.

$^1$H-NMR(CDCl$_3$): d 1.4(9H, s), 7.2–7.8(5H, m); IR(nujol): v 3300–2500, 1640 cm$^{-1}$.

b. 1-t-Butyl-4-H-3-phenyl-1,2,4-triazolin-5-one

To a stirred mixture of 381 g (1.73 mol) of benzoylformic acid t-butyl hydrazone and 1.25 L of toluene was added 184 g (1.82 mol) of triethylamine (Exotherm to 50° C.). The mixture was heated to 80° C. and 500 g (1.81 mol) of diphenylphosphoryl azide was added over 1 hour so that the internal temperature did not rise above 100° C. (Caution: N$_2$ evolution). The mixture was refluxed for 2 h, cooled to room temperature and diluted with 1 L of ether. This mixture was extracted with two 1 L portions of 5% aqueous NaOH and 500 mL of water. The combined aqueous extracts were acidified with HCl to pH 5 and stirred for 1 h. The precipitate was collected by filtration, washed with water and hexanes and dried to afford 345 g of crude product.

$^1$H-NMR(CDCl$_3$): d 1.60(9H, s), 7.2–8.0(5H, m); IR(nujol): v 1680 cm$^{-1}$ c. 1-t-Butyl-3-phenyl-4-propargyl-1,2,4-triazolin-5-one A mixture of crude 345 g (1.2 mol) of 1-t-butyl-4-H-3-phenyl-1,2,4-triazol-5-one and 3.5 L of ethyl acetate containing 0.03% water was stirred at room temperature and 190 g (1.67 mol) of solid potassium carbonate (K$_2$CO$_3$) was added. The mixture was heated at reflux for 0.5 h and 248 g (1.67 mol) of an 80% weight solution of propargyl bromide in toluene was added dropwise over 30 minutes. Refluxing was continued for an additional 3 h. The mixture was allowed to cool to room temperature, diluted with 2 L of water and stirred for 15 min. The organic layer was separated, washed with brine and dried over magnesium sulfate (MgSO$_4$). Removal of the solvent left 300 g of an oil which was crystallized from 500 mL of ether and 1500 mL of hexanes to furnish 180 g of the desired compound, mp 82°–83° C.

$^1$H-NMR: d1.65(9H, s),2.35(1H, t, J=4), 4.42(2H, d, J=4), 7.2–7.8(5H, m) IR(nujol): v 3200, 1690 cm$^{-1}$.

Examples 2, 4–6, 8–18, 20 and 33–35 were made using essentially the same procedure and substituting the appropriate starting materials such as 2-thiopheneglyoxylic acid, 2-fluorobenzoylformic acid and 3-fluorobenzoylformic acid for benzoylformic acid; methyl hydrazine, ethyl hydrazine, 2,2,2-trifluoroethyl hydrazine, n-propyl hydrazine, 2,2,3,3,tetrafluoro-(1-methyl)propyl hydrazine, cyclohexyl hydrazine, n-butyl hydrazine and isobutyl hydrazine for t-butyl hydrazine; and methyl iodide, ethyl iodide, allyl bromide, 3-methylpropargyl bromide, chloromethyl methyl ether, 2-bromoethyl methyl ether and 2-fluoroethyl bromide for propargyl bromide.

EXAMPLE 7

1-t-Butyl-3-(3-chlorophenyl)-4-ethyl-1,2,4-triazolin-5-one a. 1-(3-Chlorobenzoyl)-2-t-butyl hydrazine To a suspension of t-butyl hydrazine hydrochloride (6.2 g, 0.05 mole), water (30 mL) and toluene (60 mL) at 0° C. to 5° C. was added 50% sodium hydroxide (4.0 g, 0.05 mol). To the above reaction mixture was then added, separately and simultaneously, 50% sodium hydroxide (4.0 g, 0.05 mol) and 3-chlorobenzoyl chloride (8.8 g, 0.05 mol) from two dropping funnels. After addition was completed, the reaction mixture was stirred at 0° C. for 30 minutes and room temperature for 30 minutes. The resultant precipitate was collected by suction-filtration and washed with water (100 mL) and dried in air to give 9.0 g (79% yield) of 1-(3-chlorobenzoyl)-2-t-butyl hydrazine as a white solid. mp 116°–118° C.

b. 1-(3-Chlorobenzoyl)-2-t-butyl-4-ethyl semicarbazide

To a suspension of 1-(3-chlorobenzoyl)-2-t-butyl hydrazine (2.5 g, 0.011 mol) in ethyl ether (110 mL) was added ethyl isocyanate (0.8 g, 0.0113 mol) and a few drops of triethyl amine as a catalyst. The reaction mixture was stirred at room temperature for one hour. The resultant white precipitate was collected by suction-filtration to give 2.0 g (61% yield) of 1-(3-chlorobenzoyl)-2-t-butyl-4-ethyl semicarbazide as a white solid, mp 67°–68° C.

c. 1-t-Butyl-3-(3-chlorophenyl)-4-ethyl-1,2,4-triazolin-5-one

A solution of 1-(3-chloro-benzoyl)-2-t-butyl-4-ethyl semicarbazide (2.0 g, 0,067 mole) in 5% potassium hydroxide (40 mL) was refluxed for 20 hours, then cooled to room temperature and extracted with ethyl acetate (3×60 mL). The combined organic layers were washed with water (100 mL) and brine (100 mL), dried with sodium sulfate and filtered. The solvent was removed in vacuo to give a yellow liquid (1.2 g, 64% yield).

EXAMPLE 24

4-Ethyl-3-(3-fluorophenyl)-1-propargyl-1,2,4-triazolin-5-one a. 1-(3-Fluorobenzoyl)-4-ethyl semicarbazide To a solution of 3-fluorobenzhydrazide (5.0 g, 0.033 mol) in tetrahydrofuran (100 mL) was added ethyl isocyanate (2.6 g, 0.036 mol) at room temperature. After stirring for 24 hr, the resultant precipitate was collected by suction-filtration to give 1-(3-fluorobenzoyl)-4-ethyl semicarbazide in quantitative yield.

b. 3-(3-Fluorophenyl)-4-ethyl-1,2,4-triazolin-5-one

A mixture of the 1-(3-fluorobenzoyl)-4-ethyl semicarbazide and 1N NaOH solution (100 mL) was refluxed for 20 hr, cooled to room temperature and neutralized with conc. HCl. The suspension was extracted with ethyl acetate and the organic layer was dried over MgSO$_4$. Removal of the solvent in vacuo yielded 7.3 g of 3-(3-fluorophenyl)-4-ethyl-1,2,4-triazolin-5-one as a white solid. mp 135°–140° C.

c. 4-Ethyl-3-(3-fluorophenyl)-1-propargyl-1,2,4-triazolin-5-one

To a solution of 3-(3-fluorophenyl)-4-ethyl-1,2,4-triazolin-5-one (4 g, 0.021 mole) in dry acetone (85 mL) was added potassium carbonate (3.5 g, 0.025 mole), followed by propargyl bromide (3 g, 80% in toluene, 0.02 mole). The reaction mixture was refluxed for 20 hr. The mixture was cooled to room temperature and the solid was filtered off and washed with acetone. The filtrate was evaporated in vacuo to leave a residue which was triturated with hexane to give a light yellow solid, 3.9 g (81.4% yield), mp 57°–60° C.

Examples 19, 21, 23, 25–30, and 36–40 were made using essentially the same procedure and substituting the appropriate starting materials such as methyl isocyanate for methyl isocyanate and 3-methylbenzhydrazide, 3-chlorobenzhydrazide, 3-bromobenzhydrazide, 2-fluorobenzhydrazide, 3-methoxybenzhydrazide, 2-methoxybenzhydrazide and 2,5-dichlorobenzhydrazide for 3-fluorobenzhydrazide.

EXAMPLE 31

1-t-Butyl-4-methyl-3-phenyl-1,2,4-triazolin-5-thione

A solution of 2.24 g (11.7 mmol) of N-benzoyl-N'-t-butyl hydrazine and 0.8 mL (11.7 mmol) of methyl isothiocyanate in 5 mL of pyridine was heated at reflux for 11 h. The mixture was cooled, diluted with 175 mL of ether, washed with two 50 mL portions of 5% aqueous HCl and 50 mL of saturated aqueous NaHCO$_3$, and dried over MgSO$_4$. Removal of the solvent left 0.93 g of crude 1-t-4-methyl-3-phenyl-1,2,4-triazolin-5-thione as an oil. Flash chromatography on 30 g of silica gel eluting successively with 10, 20, 30 and 40% ether in hexanes furnished 0.58 g (20%) of pure product as an oil.

$^1$H-NMR (CDCl$_3$) d 1.86 (9H,s), 3.60 (3H,s), 7.55 (5H,m).

EXAMPLE 3 was made using essentially the same procedure and substituting N-3-trifluoromethylbenzoyl-N'-t-butyl hydrazine for N-benzoyl-N'-t-butyl hydrazine.

EXAMPLE 32

4-Ethyl-1-propyl-3-(3-thienyl)-triazolin-5-one a. 4-Ethyl-2-propyl semicarbazide To a stirred slurry of 3.35 g (20 mmol) of n-propylhydrazine oxalate and 2.24 g (20 mmol) of sodium carbonate in 50 mL of water and 10 mL of tetrahydrofuran (THF) was added 1.7 mL (21.5 mmol) of ethyl isocyanate. The mixture was stirred at room temperature for 16 h and evaporated in vacuo to leave crude 4-ethyl-2-propyl semicarbazide as a white solid.

b. 4-Ethyl-2-propyl-1-(3-thenoyl) semicarbazide

A stirred solution of 2.62 g (20.5 mmol) of thiophene-3-carboxylic acid and 2.8 mL (20.0 mmol) of triethylamine in 20 mL of THF was cooled to 5° C. and 2.6 mL (20.0 mmol) of isobutyl chloroformate was added dropwise over 5 minutes. The mixture was stirred at 5° C. for 5 minutes and added to a suspension of the 4-ethyl-2-propyl semicarbazide prepared above in 20 mL of THF at 5° C. This mixture was allowed to warm to room temperature and stirred overnight. The mixture was concentrated to remove most of the solvent, taken up in 75 mL of water and extracted with two 100 mL portions of ethyl acetate. The combined ethyl acetate extracts were washed with 50 mL of 5% aqueous HCl and 50 mL of saturated aqueous sodium bicarbonate (NaHCO$_3$), and dried over MgSO$_4$. Removal of the solvent left 5.30 g of crude 4-ethyl-2-propyl-1-(3-thenoyl) semicarbazide as an oil.

c. 4-Ethyl-1-propyl-3-(3-thienyl)-triazolin-5-one

The crude 4-ethyl-2-propyl-1-(3-thenoyl) semicarbazide was refluxed with 100 mL of 5% aqueous NaOH for 1 h. The mixture was cooled and extracted with two 100 mL portions of ether. The combined ether extracts were dried over MgSO$_4$ and concentrated to leave 0.81 g of crude 4-ethyl-1-propyl-3-(3-thienyl)-triazolin-5-one as an oil which was purified by flash chromatography on 30 g of silica gel eluting successively with 60, 80 and 100% ether in hexanes to furnish 0.65 g (14% overall) of 4-ethyl-1-propyl-3-(3-thienyl)-triazolin-5-one as an oil.

$^1$H-NMR (CDCl$_3$) d 0.95 (3H,t), 1.30 (3H,t), 1.80 (2H,m), 3.75–3.95 (4H,m) 7.4 (2H,m), 7.63 (1H,s).

EXAMPLE 22 was made using essentially the same procedure and substituting 3-chlorobenzoic acid for thiophene-3-carboxylic acid.

EXAMPLE 41

1-t-Butyl-4-(3-bromopropargyl)-3-phenyl-1,2,4-triazolin-5-one

To a solution of 1-t-butyl-4-propargyl-3-phenyl-1,2,4-triazolin-5-one (EXAMPLE 1) (1.0 g, 3.9 mmol) in acetone (30 mL) at room temperature was added N-bromosuccinimide (1.1 g, 4.9 mmol), followed by silver nitrate (0.1 g, 0.59 mmol). The reaction mixture was stirred at room temperature for 40 min. The mixture was poured into water (75 mL) and extracted with ethyl acetate (75 mL) and the organic layer was washed with water (3×50 mL) and brine (75 mL), dried over sodium sulfate and filtered. The solution was concentrated in vacuo to give 1.0 g (77% yield) of 1-t-butyl-4-(3-bromopropargyl)-3-phenyl-1,2,4-triazolin-5-one as a light yellow viscous oil which slowly solidified, mp 86°–91° C.

EXAMPLE 40 was made using essentially the same procedure and substituting N-iodosuccinimide for N-bromosuccinimide.

The compounds of the present invention are broad spectrum herbicides and may be advantageously employed to control selectively monocot and/or dicot weeds in agronomic and horticultural crops, forestry, orchards, turf, vines or for total weed control.

The compounds of the present invention are useful both as preemergence and as postemergence herbicides. Preemergence herbicides may be applied to the soil surface or incorporated into the soil. Postemergence herbicides are those which are applied after the plants have emerged and during their growth period.

The compounds of the present invention are selective or non-selective, depending on the rate applied, the combination of plants to which they are applied and whether they are applied pre- or postemergent. Such variables are understood by those skilled in the art. At higher dosage rates they tend to be non-selective, while at lower dosage rates they tend to be selective. For example, the compounds of this invention have shown selectivity preemergence and/or postemergence in crops such as, but not limited to, wheat, corn, and cotton.

The present aryl triazoles may be applied in any amount which will give the required control of weeds. A preferred rate of application of the herbicides of the invention is from about 0.001 to about 12 pounds per acre and especially preferred from about 0.01 to about 5 pounds of the aryl triazole per acre. Most preferably, a rate from about 0.02 to about 2 pounds per acre is used.

The aryl triazoles of the present invention may be applied to the soil surface prior to plant emergence or incorporated into the soil or other growth medium prior to planting. This incorporation can be carried out by any convenient means, including by simply mixing with the soil, by applying the aryl triazole to the surface of the soil and then disking or dragging into the soil to the desired depth, or by employing a liquid carrier to accomplish the necessary penetration and impregnation.

An aryl triazole of the present invention can be applied postemergence to plants to be treated or to the growth medium either by itself, or, as is generally done, as a component in a herbicidal composition or formulation which also comprises an agronomically acceptable carrier. The concentration of the aryl triazole in the herbicidal composition can vary from about 1% to about 98%.

By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the aryl triazoles of the present invention may also be used in any of these herbicidal formulations. The herbicidal compositions of the invention can be either solid or liquid formulations or solutions. For example, the aryl triazoles can be formulated as wettable powders, solutions, emulsifiable concentrates, dusts, granular formulations, aerosols, water dispersable granular formulations or flowable concentrates as is known to one skilled in the art. In such formulations, the compounds are extended with a liquid or solid carrier and, when desired, suitable surfactants are incorporated. Examples of solvents which are useful in the practice of this invention include alcohols, ketones, aromatic hydrocarbons, halogenated hydrocarbons, dimethylformamide, dioxane, dimethyl sulfoxide, and the like.

It is usually desirable, particularly in post-emergence applications, to include spray adjuvants such as wetting agents, spreading agents, dispersing agents, sticking agents, surfactants, adhesives, and the like, in accordance with agricultural practices. Examples of adjuvants which are commonly used in the art can be found in the John W. McCutcheon, Inc. publication "Detergents and Emulsifiers Annual".

The aryl triazoles of the present invention can also be mixed with fertilizers or fertilizing materials before their application. In one type of solid fertilizing composition in which the aryl triazoles may be used, particles of a fertilizer or fertilizing ingredients, such as ammonium sulfate, ammonium nitrate, or ammonium phosphate can be coated with one or more of the aryl triazoles. The solid aryl triazole and solid fertilizing material may also be admixed in blending or mixing equipment, or they can be incorporated with fertilizers in granular formulations. Any relative proportion of aryl triazole and fertilizer can be used which is suitable for the crops and weeds to be treated.

The aryl triazoles of the present invention may be applied to herbicidal sprays by methods commonly employed, such as conventional high-gallonage hydraulic sprays, low gallonage sprays, air blast spray, aerial sprays and dusts.

For some applications, one or more other herbicides may be added to the aryl triazoles of the present invention, thereby providing additional advantages and effectiveness. When mixtures of herbicides are employed, the relative proportions which are used will depend upon relative efficacy of the compounds in the mixture with respect to the plants to be treated. Examples of other herbicides which can be combined with the aryl triazoles of the present invention include:

Carboxylic Acids and Derivatives 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;
2,3,6-trichlorophenylacetic acid and its salts;
3,6-endoxohexahydrophthalic acid and its salts;
dimethyl 2,3,5,6-tetrachloroterephthalate;
trichloroacetic acid and its salts;
2,2-dichloropropionic acid and its salts;
2,3-dichloroisobutyric acid and its salts;
isopropylammonium 2-(4-isopropyl-4-methyl-5-oxo-2-imidazolin-2-yl)nicotinate;
2-[4,5-dihydro-4-methyl-4- (1-methylethyl)-5-oxo-1H-imidazol-2-yl]3-quinolinecarboxylic acid;
m-toluic acid, 6-(4-isopropyl-4-methyl-5-oxo-2-imidazolin-2-yl)-methyl ester and p-toluic acid, 6-(4-isopropyl-4-methyl-5-oxo-2-imidazolin-2-yl)-methyl ester;
N-(phosphonomethyl)glycine, isopropylammonium salt;
[3,5,6-trichloro-(2-pyridinyl)oxy]acetic acid;
3,7-dichloro-8-quinolinecarboxylic acid;
ammonium dl-homoalanin-4-yl(methyl)phosphinate;

Carbamic Acid Derivatives ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;
N-methyldithiocarbamic acid salts;
ethyl 1-hexamethyleneiminecarbothiolate;
isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts;
S-(4-chlorobenzyl )-N,N-diethylthiolcarbamate;

Substituted Ureas 2-chloro-N-[(4-methoxy-6-methyl-1,3,5-triazin-2-yl)aminocarbonyl]benzenesulfonamide;
3-(3,4-dichlorophenyl )-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)diethylurea;
dichloral urea;
methyl 2-[[[[(4,6-dimethyl-2-pyrimidinyl)amino]carbonyl]amino]sulfonyl]benzoate;
N-((6-methoxy-4-methyl-1,3,5- triazin-2-yl) aminocarbonyl)-2-(2-chloroethoxy)benzenesulfonamide;
2-[[[(4-chloro-6-methoxypyrimidine-2-yl)aminocarbonyl]amino]sulfonyl]benzoic acid, ethyl ester;
methyl 2-[[[[(4-methoxy-6-methyl-1,3,5-triazin-2-yl)amino]carbonyl]amino]sulfonyl]benzoate
methyl 3-[[[[(4-methoxy-6-methyl-1,3,5-triazin-2-yl)amino]carbonyl]amino]sulfonyl]2-thiophenecarboxylate;
methyl 2-[[[[[(4,6-dimethoxypyrimidin-2-yl)amino]carbonyl]amino]sulfonyl]methyl]benzoate;
methyl 2-[[[[(4-methoxy-6-methyl-1,3,5-triazin-2-yl)methylamino]carbonyl]amino]sulfonyl]benzoate;

Substituted Triazines 2-chloro-4,6-bis(ethylamino)-s-triazine;
2-chloro-4-ethylamino-6-isopropylamino-s-triazine;
2-chloro-4,6-bis(methoxy-n-propylamino)-s-triazine;
2-methoxy-4,6-bis(isopropylamino)-s-triazine;
2-chloro-4-ethylamino-6-(3 -methoxy-n-propylamino)-s-triazine;
2-methylmercapto-4,6-bis(isopropylamino)-s-triazine;
2-methylmercapto-4,6-bis(ethylamino)-s-triazine;
2-methylmercapto-4-ethylamino-6-isopropylamino-s-triazine;
2-chloro-4,6-bis(isopropylamino)-s-triazine;
2-methoxy-4,6-bis(ethylamino)-s-triazine;
2-methoxy-4-ethylamino-6-isopropylamino-s-triazine;
-methylmercapto-4-(2-methoxyethylamino)-6-isopropylamino-s-triazine;
4-amino-6-(t-butyl)-3-(methylthio)-1,2,4-triazine-5(4H)-one;

Diphenyl Ether Derivatives 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-4'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1-(3-ethoxy-4-nitrophenoxy)-4-(trifluoromethyl)benzene;
1-(carboethoxy)ethyl 5-[2-chloro-4-(trifluoromethyl)-phenoxy]2-nitrobenzoate;
5-[2-chloro-4-(trifluoromethyl)phenoxy]N-(methylsulphonyl)-2-nitrobenzamide;

Anilides 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-alpha,alpha-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

Oxyphenoxy Herbicides 2-(4-(2,4-dichlorophenoxy)phenoxy)methyl propionate;
methyl 2-(4-(3-chloro-5-(trifluoromethyl)-2-pyridinyloxy)phenoxy)propanoate;
butyl (R)-2-[4-[5-(trifluoromethyl)-2-pyridinyloxy]-phenoxy]propionate;
ethyl 2-[4-[(6-chloro-2-benzoxazolyl)oxy]phenoxy]propanoate;
butyl 2-[4-[[5-(trifluoromethyl)-2-pyridinyl]oxy]phenoxy]propionate;
2-[4-[(6-chloro-2-quinoxalinyl)oxy]phenoxy]propionic acid, ethyl ester;

Uracils 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

Nitriles 2,6-dichlorobenzonitrile; diphenylacetonitrile;
3,5-dibromo-4-hydroxybenzonitrile;
3,5-diiodo-4-hydroxybenzonitrile;

Other Organic Herbicides 2-chloro-N,N-diallylacetamide;
N-(1,1-dimethyl-2-propynyl)-3,5-dichlorobenzamide;
maleic hydrazide;
3-amino-1,2,4-triazole;
monosodium methanearsonate;
disodium methanearsonate;
N,N-dimethyl-alpha,alpha-diphenylacetamide;
N,N-di(n-propyl)-2,6-dinitro-4-(trifluoromethyl)aniline;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;

4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1'-c]pyrazidiium salts;
1,1'-dimethyl-4,4'-bipyridinium salts;
3,4,5,6-tetrahydro-3,5-dimethyl-2-thio-2-H-1,3,5-thiadiazine;
2-[1-(ethoxyimino)butyl]5-[2-(ethylthio)propyl]3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-(α,α,α-trifluoro-m-toluyl)-3(2H)-pyridazinone;
2-(3,5-dichlorophenyl)-2-(2,2,2-trichloromethyl)oxirane.

The herbicidal activity of aryl triazoles of the present invention towards a number of common weeds was evaluated using a greenhouse method of testing. Using the procedures described below, the aryl triazoles of the present invention were evaluated for control of the following weeds:

|  | Monocots |
|---|---|
| Barnyardgrass (BYG) | *Echinochloa crus-galli* |
| Foxtail (FOX) | *Setaria viridis* |
| Johnsongrass (JON) | *Sorghum halepense* |
| Nutsedge (NUT) | *Cyperus esculentus* |
| Wild Oat (WO) | *Avena fatua* |
|  | Dicots |
| Cocklebur (CKL) | *Xanthium strumarium* |
| Morningglory (MG) | *Ipomoea lacunosa* |
| Pigweed (PIG) | *Amaranthus retroflexus* |
| Smartweed (SMT) | *Polygonum lapathifolium* |
| Velvetleaf (VEL) | *Abutilon theophrasti* |

The following test procedure was employed. Seeds of selected plants were planted in flats or pots. For preemergence tests, immediately after planting, the test compound was sprayed directly onto the soil surface. The flats or pots were then watered. For postemergence tests, the seeds were allowed to germinate and grow for 10 to 21 days. Each series of test plants were selected for uniformity, size, and stage of development. The test plants were then treated with the test compound.

The compound to be evaluated was dissolved in an appropriate solvent, usually acetone, and sprayed over the flats or pots using a carrier volume equivalent to 25 or 50 gallons per acre at the rate of application in pounds per acre (lb./A) specified in the table. About two or three weeks after application of the test compound, the state of growth of the plant was observed. Each species was evaluated on a scale of 0–100 in which 0 equals no activity and 100 equals total control. The following table (Table III) shows the results obtained for the test compounds at the stated rate of application.

TABLE III

| Cmpd No | APPL TYPE | CKL | MG | PIG | SMT | VEL | BYG | FOX | JON | NUT | WO |
|---|---|---|---|---|---|---|---|---|---|---|---|
| HERBICIDAL ACTIVITY | | | | | | | | | | | |
| 1. | PRE | 0 | 100 | 100 | 100 | 100 | 97 | 100 | 97 | 97 | 97 |
|  | POST | 10 | 57 | 90 | 90 | 37 | 87 | 100 | 77 | 0 | 27 |
| 2. | PRE | 0 | 0 | —* | 100 | 67 | 87 | 100 | 97 | 0 | 37 |
|  | POST | 0 | 27 | 100 | 0 | 20 | 10 | 90 | 25 | 0 | 10 |
| 3. | PRE | 0 | 0 | 0 | 0 | 0 | 0 | 0 | 0 | — | 0 |
|  | POST | 0 | 51 | 100 | 0 | 11 | 0 | 0 | 0 | 0 | 0 |
| 4. | PRE | 0 | 100 | — | — | 100 | 97 | 100 | 87 | 100 | 97 |
|  | POST | 0 | 45 | 0 | 0 | 15 | 10 | 0 | 15 | 0 | 0 |
| 5. | PRE | 0 | 37 | 100 | — | 47 | 97 | 100 | 87 | 0 | 97 |
|  | POST | 0 | 35 | 100 | 0 | 10 | 0 | 0 | 0 | 0 | 0 |
| 6. | PRE | 0 | 0 | 0 | 0 | 0 | 37 | 77 | 17 | 0 | 17 |
|  | POST | 5 | 80 | 0 | 0 | 0 | 0 | 0 | 0 | 0 | 0 |
| 7. | PRE | 0 | 0 | 100 | 57 | 17 | 37 | 57 | 37 | 0 | 17 |
|  | POST | 0 | 27 | 5 | 7 | 0 | 0 | 0 | 10 | 0 | 0 |
| 8. | PRE | 0 | 98 | 100 | 100 | 100 | 100 | 100 | 99 | 87 | 95 |
|  | POST | 20 | 45 | 77 | 47 | 47 | 47 | 90 | 20 | 0 | 67 |
| 9. | PRE | 0 | 77 | 100 | 90 | 100 | 100 | 100 | 37 | 0 | 97 |
|  | POST | 0 | 67 | 0 | 5 | 5 | 0 | 0 | 0 | 0 | 0 |
| 10. | PRE | 0 | 70 | 100 | 100 | 100 | 100 | 100 | 97 | 67 | 100 |
|  | POST | 0 | 90 | 25 | 80 | 30 | 37 | 10 | 20 | 0 | 0 |
| 11. | PRE | 67 | 100 | 100 | 100 | 100 | 100 | 100 | 100 | 97 | 100 |
|  | POST | 0 | 85 | 67 | 37 | 37 | 77 | 25 | 87 | 0 | 27 |
| 12. | PRE | 67 | 100 | 100 | 100 | 100 | 100 | 100 | 100 | 57 | 100 |
|  | POST | 0 | 37 | 77 | 57 | 27 | 57 | 20 | 37 | 0 | 0 |
| 13. | PRE | 27 | 100 | 100 | 100 | 100 | 100 | 100 | 100 | 97 | 100 |
|  | POST | 51 | 50 | 100 | 90 | 77 | 95 | 100 | 100 | 47 | 87 |
| 14. | PRE | 0 | 85 | 100 | 100 | 90 | 98 | 99 | 95 | 100 | 80 |
|  | POST | 0 | 55 | 25 | 10 | 0 | 0 | 0 | 0 | 0 | 0 |
| 15. | PRE | 0 | 0 | 0 | 0 | 0 | 45 | 55 | 10 | 0 | 0 |
|  | POST | 0 | 35 | 0 | 0 | 0 | 0 | 0 | 0 | 0 | 0 |
| 16. | PRE | 5 | 70 | 100 | 100 | 100 | 98 | 98 | 99 | 10 | 85 |
|  | POST | 15 | 45 | 10 | 70 | 40 | 90 | 70 | 15 | 0 | 25 |
| 18. | PRE | 5 | 100 | 100 | 100 | 80 | 98 | 99 | 98 | 99 | 98 |
|  | POST | 10 | 0 | 0 | 20 | 0 | 30 | 20 | 0 | 0 | 10 |
| 19. | PRE | 0 | 90 | 100 | 100 | 90 | 100 | 100 | 98 | 0 | 20 |
|  | POST | 0 | 20 | 15 | 25 | 0 | 0 | 0 | 0 | 0 | 0 |
| 20. | PRE | 15 | 100 | 100 | 100 | 100 | 98 | 98 | 99 | 99 | 98 |
|  | POST | 5 | 30 | 90 | 60 | 45 | 75 | 0 | 10 | 20 | 10 |
| 21. | PRE | 0 | 10 | 100 | 100 | 90 | 98 | 100 | 0 | 0 | 20 |
|  | POST | 0 | 0 | 0 | 0 | 0 | 0 | 0 | 0 | 0 | 0 |

TABLE III-continued
HERBICIDAL ACTIVITY

| Cmpd No | APPL TYPE | CKL | MG | PIG | SMT | VEL | BYG | FOX | JON | NUT | WO |
|---|---|---|---|---|---|---|---|---|---|---|---|
| 22. | PRE | 0 | 20 | 100 | 98 | 25 | 100 | 75 | 10 | 10 | 15 |
|  | POST | 0 | 10 | 0 | 0 | 0 | 0 | 15 | 0 | 0 | 10 |
| 23. | PRE | 100 | 100 | 100 | 100 | 100 | 100 | 100 | 100 | 55 | 100 |
|  | POST | 0 | 15 | 10 | 20 | 15 | 35 | 20 | 0 | 0 | 0 |
| 24. | PRE | 100 | 100 | 100 | 100 | 100 | 100 | 100 | 100 | 70 | 100 |
|  | POST | 0 | 40 | 20 | 25 | 15 | 0 | 25 | 0 | 0 | 0 |
| 25. | PRE | 0 | 85 | 100 | 75 | 20 | 100 | 100 | 0 | 0 | 15 |
|  | POST | 0 | 20 | 20 | 10 | 0 | 0 | 0 | 0 | 0 | 0 |
| 26. | PRE | 0 | 100 | 100 | 100 | 100 | 100 | 100 | 90 | 20 | 50 |
|  | POST | 0 | 20 | 35 | 30 | 15 | 0 | 0 | 0 | 0 | 0 |
| 27. | PRE | 0 | 45 | 100 | 85 | 15 | 85 | 98 | 10 | 0 | 20 |
|  | POST | 0 | 0 | 15 | 20 | 15 | 0 | 0 | 0 | 0 | 0 |
| 28. | PRE | 0 | 20 | 90 | 98 | 15 | 100 | 95 | 0 | 0 | 95 |
|  | POST | 0 | 0 | 15 | 15 | 0 | 0 | 10 | 0 | 0 | 0 |
| 29. | PRE | 0 | 100 | 100 | 100 | 100 | 100 | 100 | 99 | 10 | 55 |
|  | POST | 0 | 10 | 35 | 35 | 0 | 20 | 0 | 0 | 0 | 0 |
| 30. | PRE | 0 | 15 | 90 | 15 | 15 | 50 | 10 | 0 | 0 | 10 |
|  | POST | 0 | 65 | 25 | 10 | 0 | 0 | 0 | 0 | 0 | 0 |
| 31. | PRE | 0 | 0 | 90 | 90 | 0 | 25 | 80 | 0 | 0 | 0 |
|  | POST | 0 | 0 | 0 | 0 | 0 | 0 | 0 | 0 | 0 | 0 |
| 32. | PRE | 0 | 0 | 25 | 98 | 15 | 0 | 0 | 0 | 0 | 10 |
|  | POST | 0 | 0 | 0 | 0 | 10 | 0 | 40 | 0 | 0 | 10 |
| 33. | PRE | 0 | 0 | 100 | 20 | 70 | 0 | 20 | 0 | 0 | 0 |
|  | POST | 0 | 0 | 15 | 0 | 0 | 0 | 0 | 0 | 0 | 0 |
| 34. | PRE | 0 | 100 | 100 | 100 | 100 | 100 | 100 | 100 | 70 | 100 |
|  | POST | 10 | 70 | 70 | 60 | 35 | 85 | 100 | 75 | 0 | 15 |
| 35. | PRE | 0 | 35 | 100 | 100 | 100 | 100 | 100 | 100 | 35 | 80 |
|  | POST | 0 | 20 | 30 | 95 | 15 | 98 | 95 | 20 | 15 | 60 |
| 36. | PRE | 0 | 0 | — | 35 | 0 | 90 | 65 | 0 | 0 | 15 |
|  | POST | 0 | 0 | 0 | 0 | 0 | 0 | 0 | 0 | 0 | 0 |
| 37. | PRE | 0 | 0 | — | 0 | 0 | 75 | 25 | 0 | 0 | 0 |
|  | POST | 0 | 0 | 0 | 0 | 0 | 0 | 0 | 0 | 0 | 0 |
| 38. | PRE | 0 | 0 | — | 100 | 15 | 95 | 15 | 0 | 0 | 0 |
|  | POST | 0 | 0 | 0 | 0 | 0 | 0 | 0 | 0 | 0 | 0 |
| 39. | PRE | 0 | 0 | — | 0 | 0 | 60 | 80 | 20 | 25 | 10 |
|  | POST | 0 | 20 | 40 | 20 | 0 | 0 | 0 | 0 | 0 | 0 |
| 40. | PRE | 0 | 0 | 100 | 25 | 0 | 77 | 100 | 17 | 0 | 0 |
|  | POST | 0 | 0 | 10 | 0 | 0 | 0 | 0 | 0 | 0 | 0 |
| 41. | PRE | 0 | — | 100 | 97 | 100 | 100 | 100 | 97 | 67 | 97 |
|  | POST | 7 | 7 | 17 | 97 | 17 | 77 | 77 | 37 | 0 | 37 |

*— = Not tested.

It is to be understood that changes and variations may be made without departing from the spirit and scope of the invention as defined by the appended claims.

What is claimed is:

1. A compound of the formula

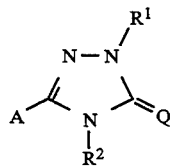

wherein
A is phenyl or substituted phenyl with one or two substituents independently selected front ($C_1$-$C_3$)alkyl, halogen, methoxy or trifluoromethyl;
Q is oxygen or sulfur; and
(a) $R^1$ is ($C_3$-$C_6$)alkenyl and $R^2$ is ($C_1$-$C_2$)alkyl, ($C_3$-$C_6$)alkynyl, monohalo ($C_1$-$C_6$)alkyl, monohalo ($C_3$-$C_6$)alkynyl, or ($C_1$-$C_6$)alkoxy ($C_1$-$C_6$)alkyl;
or
(b) $R^1$ is ($C_1$-$C_2$)alkyl, ($C_3$-$C_6$)alkynyl, monohalo ($C_1$-$C_6$)alkyl, monohalo ($C_3$-$C_6$)alkynyl, or ($C_1$$C_6$)alkoxy ($C_1$-$C_6$)alkyl; and $R^2$ is ($C_3$-$C_6$)-alkenyl;
or
(c) $R^1$ and $R^2$ are each independently selected from ($C_3$-$C_6$)alkenyls.

2. A compound of the formula

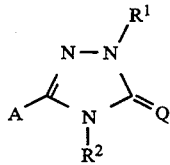

wherein
A is thienyl or substituted thienyl with one or two substituents independently selected from ($C_1$-$C_3$)alkyl, halogen, methoxy or trifluoromethyl;
Q is oxygen or sulfur; and
$R^1$ and $R^2$ are independently selected from ($C_3$-$C_6$)alkenyl, ($C_3$-$C_6$)alkynyl; monohalo($C_3$-$C_6$)alkynyl or ($C_1$-$C_6$)alkoxy ($C_1$-$C_6$)alkyl.

* * * * *